United States Patent
Renieri et al.

(10) Patent No.: US 6,935,197 B2
(45) Date of Patent: Aug. 30, 2005

(54) METHOD AND APPARATUS FOR TESTING UNCURED PREPREG MATERIAL

(75) Inventors: Gary D Renieri, Chesterfield, MO (US); Steven J. Burpo, Hawk Point, MO (US); Neal A. Froeschner, Florissant, MO (US); James M. Ogonowski, Chesterfield, MO (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 10/765,436

(22) Filed: Jan. 26, 2004

(65) Prior Publication Data

US 2005/0160829 A1    Jul. 28, 2005

(51) Int. Cl.[7] ............................................... G01L 1/00

(52) U.S. Cl. ................................................ 73/862.541

(58) Field of Search ...................... 73/862.07, 862.381, 73/862.391, 862.42, 862.453, 862.541, 862.621, 73/729.1, 730

(56) References Cited

U.S. PATENT DOCUMENTS

| | | | | |
|---|---|---|---|---|
| 4,592,795 A | * | 6/1986 | Bridgeford | 156/203 |
| 5,068,142 A | * | 11/1991 | Nose et al. | 442/50 |
| 6,555,488 B1 | * | 4/2003 | Qiu et al. | 442/205 |
| 6,811,638 B2 | * | 11/2004 | Close et al. | 156/164 |

* cited by examiner

*Primary Examiner*—William Oen
(74) *Attorney, Agent, or Firm*—Shaukat A. Karjeker; Steiner Norris, PLLC

(57) ABSTRACT

The invention provides an apparatus and method for testing the tensile load bearing properties of a sample of uncured prepreg composite material. The apparatus includes a housing comprising an internal cavity for receiving a sample to be tested. It also has a bladder and a block located at least partially within the housing such that inflating the bladder applies pressure to the prepreg sample by urging the block into the sample cavity, against the sample. In addition, the apparatus includes a heater for applying controlled heat to the sample and thermocouples for measuring sample temperature. Ends of the sample prepreg are accessible to jaws of a tensile load testing machine, and load is applied when the desired temperature and pressure are obtained.

19 Claims, 2 Drawing Sheets

| PRESSURE | TEMPERATURE | YIELD POINT PSI | AVE. |
|---|---|---|---|
| 100 PSI | 250 °F | 190, 220, 320 | 243 |
| 50 PSI | 250 °F | 240, 260, 260 | 253 |
| 25 PSI | 250 °F | 130, 130, 190 | 150 |

METHOD AND APPARATUS FOR TESTING UNCURED PREPREG MATERIAL

BACKGROUND OF THE INVENTION

1. Field of the Invention

The invention relates to the field of materials testing, and more particularly to the testing of properties of composite materials.

2. Description of the Related Art

Composite materials are becoming increasingly important in a variety of applications, as processes for manufacture improve and as properties of these materials are better understood, and hence more readily customized for particular uses. Composites generally include a solid material (a filler or reinforcement that could be fine, fibrous, or a woven or nonwoven oriented or non-oriented fiber material, etc.) incorporated into a matrix that most typically is an organic polymer. The matrix and filler combination is known as a "prepreg", before the matrix polymer is crosslinked. Additives of various kinds may be added to serve a variety of functions. In its simplest aspect, engineering the properties of the composite depends upon appropriate selection of the solid material and the matrix material. Such engineered composites are used in the aerospace industry in a variety of structural applications, and are also finding use in other areas, for example the automobile industry, because they can be made lightweight, strong, and durable.

It is generally desirable to know what the properties of an engineered composite are before it is used in a commercial or other application. Ordinarily, this can be determined by taking a sample of the cured material, often referred to as a "coupon", and testing the sample for those properties deemed critical or important.

SUMMARY OF THE INVENTION

The invention includes an apparatus and method of using the apparatus to test properties of an uncured prepreg. As a consequence, the invention provides several significant advantages and benefits. Among these are the capability to rapidly and effectively test a range of prepreg samples to determine how the prepregs would perform when pressed in a full scale forming tool, and in particular, to reliably predict flow properties of the prepregs in the tools. As a result, the invention provides savings in materials, labor and time that would otherwise be expended in forming full scale composites on tools from the prepregs, and only thereafter determining the composite properties fail to meet requirements, and it must be rejected. Further, by facilitating rapid testing of small test prepreg samples, the invention permits the testing of a range of prepregs samples and hence the possibility of optimizing prepreg selection for forming of specific full scale composites.

In one embodiment, the invention provides an apparatus for testing the tensile load bearing properties of a sample of an uncured prepreg composite material that includes at least the following components:

(a) a housing containing an internal cavity for receiving a sample to be tested;
(b) a bladder located within the housing adjacent an inner side of the housing such that a face of the bladder extends substantially coextensively along that side when the bladder is inflated;
(c) a substantially rectangular block within the housing, one side of the block extending substantially coextensively with the bladder, when the bladder is inflated; and an opposite side of the block urged by the bladder towards the cavity, as the bladder is inflated, to thereby apply pressure to a sample in the cavity, when the apparatus is in use.

In addition, the apparatus includes a heater for applying controlled heat to a sample in the cavity, when the apparatus is in use, and thermocouples for measuring sample temperature.

In general, the each of the opposite ends of the sample are accessible to a jaw of a tensile load measuring apparatus, and tensile load is applied when the sample has been pressurized to the desired pressure, and the heated to the desired temperature for the test. The test generates a load vs. deflection curve that can be used to determine flow properties of the prepreg at test conditions, and thus to predict flow properties of a full sized prepreg when formed in a tool.

The invention also provides, in another embodiment, a method of using the test apparatus. Briefly, the method includes testing of a property of an uncured prepreg sample by:

(d) selecting an uncured prepreg sample to be tested;
(e) preparing the sample, including optionally applying a release film to the sample;
(f) subjecting the sample to heat and pressure in an apparatus comprising: a housing sized for at least partially containing the sample to be tested; an expandable bladder at least partially contained in the housing, the bladder applying controlled pressure against a block which in turn transmits applied pressure to the sample; and a heater configured to supply controlled heat to the sample;
(g) measuring a temperature of the sample;
(h) applying tensile force to the sample; and
(i) determining the tensile load at which the sample yields.

The foregoing represents a brief summary of advantages and features of the invention that is detailed in the discussion here below and from which a person of skill in the art will readily appreciate additional benefits and features of the invention.

BRIEF DESCRIPTION OF THE DRAWINGS

The following illustrative diagrams are not to scale, and are intended to facilitate an understanding of the invention. The diagrams do not limit the scope of the invention, which is demarcated solely in the claims here below.

The foregoing diagrams should be understood in light of the more detailed description of embodiments of the invention provided in the following section.

DETAILED DESCRIPTION OF THE PREFERRED EMBODIMENTS

In the specification and claims, the term "prepreg" means a material that is a combination of a filler, of any kind, coated with or contained in a matrix, that is typically formed of a an organic polymer. The term "uncured" to describe the prepreg means that the matrix polymer is not cured.

The method and apparatus of the invention are applicable to uncured prepregs of all kinds, and particularly to prepregs that have discontinuous fiber filler. The term "discontinuous" as used in the specification and claims means that the fiber does not generally extend from end to end of the prepreg along the length subject to tensile load in testing, although some individual fibers might be sufficiently long to so extend. An example of discontinuous fibers include IM7-SBCF/M73 sold by Hexcel Corp of Utah.

The term "release film" as used in the specification and claims means a type of material that can be interposed between two bodies to prevent adhesion between the two, when they are subjected to heat and pressure. A variety of release films are commercially available, for example CHR-6 sold by Furon Corp. of New York State.

The invention solves a problem that is herein identified. During pressing of a prepreg on a tool under heat and pressure into a composite, flow properties of the prepreg play a significant role in determining whether the resultant composite meets specifications, or is rejected. Acceptable composite could be identified more efficiently, and the reject rate could be significantly reduced, resulting in savings on materials, time and labor, if flow properties were determined before full scale composite formation. Moreover, composites could be optimized if it were possible to prepare several prepreg variations, and test each without having to make full scale prepregs for composite formation. The invention provides an apparatus and method that solves the aforementioned problem and allows optimization of prepreg selection.

In accordance with the invention there is provided a method and apparatus for testing the load vs. deflection property of uncured prepreg samples. The invention is applicable to virtually any kind of prepreg sample regardless of matrix or filler type or composition, and regardless of additives in the prepreg. By providing for the testing of small sized samples of prepregs, in a rapid and repeatable manner, the invention enables an optimization capability that was not available heretofore. Information developed from the tests can be used in the forming of full scale composites from prepregs, because important flow properties and characteristics of the prepregs are known prior to pressing the prepregs.

Figure 1:
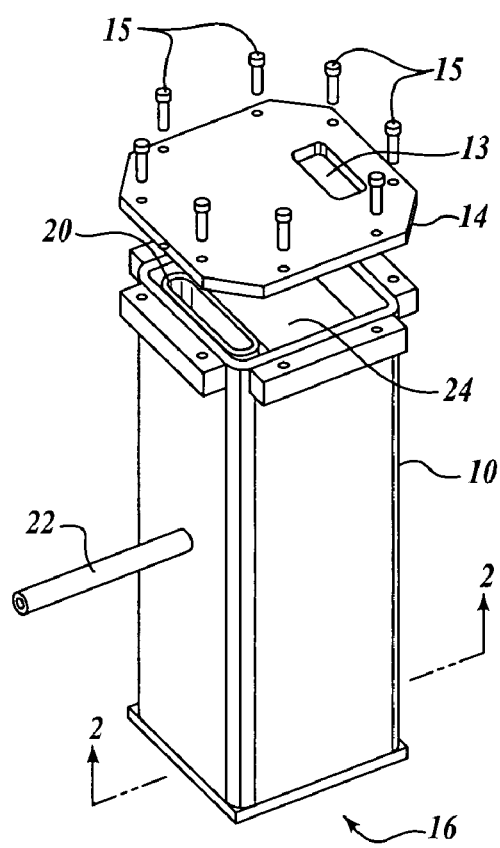
FIG. 1 is a schematic perspective view showing external details and some internal details of an embodiment of the test apparatus of the invention.
Figure 2:
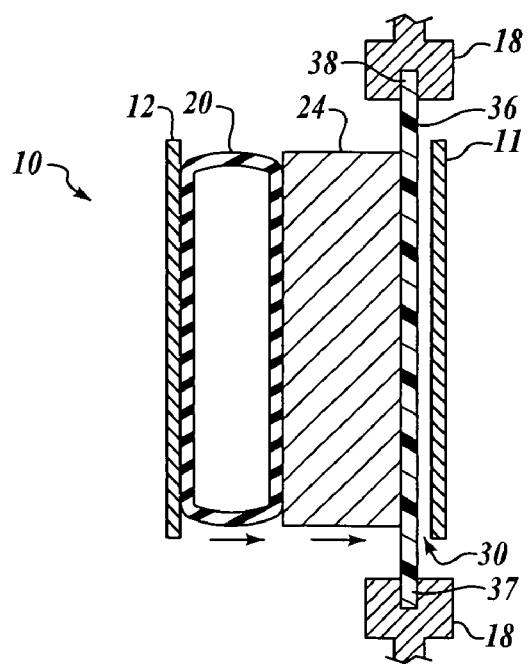
FIG. 2 is a schematic longitudinal cross sectional view taken at 2—2 of FIG. 1, showing internal structure of an embodiment of the test apparatus of the invention, with a test sample inserted.

A better understanding of the apparatus of the invention might be facilitated with reference to the appended diagrams that represent embodiments of the invention. Referring to FIGS. 1 and 2, the test apparatus has an outer housing 10, shown in this particular embodiment as a rectangular box, with its longest dimension along the vertical axis. The housing 10 has a top 14, that is applied with bolts 15. Likewise, the housing 10 has a base 16, like the top 14, applied with bolts, not shown. The top 14 and base 16 are each supplied with a slot 13 through which opposite ends 37, 38 of a prepreg 34 undergoing testing will extend for gripping by jaws 18 of a tensile stress apparatus (not shown).

The interior of the housing 10 contains at least partially, and in the embodiment shown completely, an inflatable bladder 20 and a block 24, that is urged by the inflating bladder to apply pressure to the cavity 30. The bladder 20 is located adjacent to one side of the housing 10, and is inflated via its fill line 22 with a suitable fluid. When the bladder is inflated, as shown in FIG. 2, it abuts against the inner wall 12 of the housing 10 and is substantially coextensive with that inner wall 12. The opposite side of bladder 20 abuts and urges the side of the block 24, which is preferably, but not necessarily, an aluminum block, and that is sized to at least be as long and as wide as the test sample 36 so as to provide pressure to the entire surface of the sample, when it is urged against the sample. Thus, in operation, when the bladder 30 is inflated by pressurizing its interior with water or another fluid in a controlled manner, it expands and urges the block 24 into the cavity 30 in which the test sample 36 is held. The bladder 20 is inflated until the block 24 presses against the test sample 36 pressing it against opposite inner wall 11 of the housing 10 thereby applying pressure uniformly along the length of the sample. This pressure is readily measured since it is the same as the pressure applied to the bladder 20 interior by the inflating fluid. The application of pressure can be effected in a variety of ways, for example through use of a pump and control valve, in the case of hydraulic pressure. A pressure gauge measures the applied pressure. Pressure applied will vary by type of prepreg, but is typically in a range around the pressure that it is expected would have to be applied to form the prepreg in a tool. Typical pressures are in the range 50 psi to 2000 psi, but in some cases pressures outside this range may also be useful. Desirably, for cost reasons, using the lowest useful pressure is better, unless other factors dictate differently.

The apparatus also applies heat to the test sample 36 to achieve a desired temperature. The temperature desired should be that range of temperatures at which the matrix polymer is at its lowest viscosity for ease of forming of the prepreg into a composite. Typically, the viscosity of a polymer decreases as temperature increases, and then substantially levels off so that there is a range of temperatures within which viscosity is maintained within a range. Once temperature exceeds this range, polymer crosslinking might commence at rates sufficient to cause apparent viscosity increase to occur. It is therefore desirable to remain within the range of temperatures where viscosity is at or near its lowest point.

Figures 3, 4:
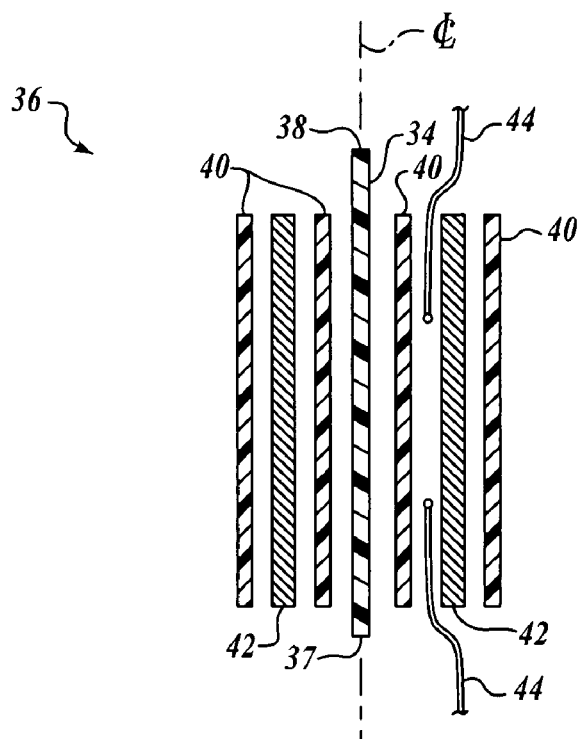
FIG. 3 is a schematic longitudinal cross sectional view of an embodiment of test sample useful in the invention showing the prepreg, release film and heating tape arrangement.
FIG. 4 is a Table of test results obtained using an embodiment of the invention.

Tensile load is applied as soon as temperature and pressure conditions are achieved, to minimize effects caused by potential cross linking of the polymer matrix. The tensile load is best measured in force per linear inch of the width of the sample, i.e. the dimension at right angles to applied force. If the sample is not rectangular but has an irregular width that varies, which is not preferred, then the smallest width is used. As shown in the embodiment of FIG. 3, a test sample 36 might include several components surrounding the uncured prepreg 34 to be tested. In this instance, the prepreg 34 is first surrounded by a release film 40 over which is applied heating tape 42. The release film 40 prevents adhesion of the prepreg 34 to the heating tape 42 during the test if the prepreg 34 begins to flow. Further, to prevent the block 24 from adhering to the tape, in case of prepreg flow leaks, a second precautionary release film 40 is applied around the prepreg/heating tape combination. By regulating current flow to the heating tape, the rate of heat energy applied to the sample can be regulated. In order to measure the prepreg temperature, thermocouples 44 may be included in the test sample adjacent to or in contact with the prepreg 34. Typical temperatures may be in the range 100° F. (38° C.) to 350° F. (177° C.), although temperatures outside this range may also be useful in specific instances.

Referring to FIG. 3, the ends 37, 38 of the uncured prepreg extend beyond the heating tape 42 and release films so as to be accessible to the jaws 18 of the tensile load measuring machine. Once temperature and pressure conditions are achieved, tensile load is applied to the prepreg 34 until the sample yields. The yield point load is then recorded and this provides insight into the flow of the prepreg in a forming tool under similar temperature and pressure conditions.

The following example illustrates aspects of the invention described herein and does not limit the scope of the invention.

EXAMPLE

One inch wide prepreg test samples were prepared for testing in an apparatus like that illustrated in FIGS. 1–2 above. The prepregs included IM7 fiber, a product of Hexcel Corporation of Utah) embedded in a matrix epoxy polymer (M73, a product of Hexcel of Utah). Each of the nine samples was individually placed in the test apparatus, and desired temperature and pressure conditions were obtained before a tensile load was applied. Hydraulic pressure was applied to the prepreg by pumping water into the bladder of the apparatus. The temperature was controlled by wrapping each prepreg in a release film, and applying a heating tape and supplying thermocouples, substantially as shown in FIG. 3. The yield point of each prepreg was recorded from the tensile load machine. Results are summarized in the Table of FIG. 4.

Each of the tests was carried out at 250° F. (121° C.). From the results it is apparent that as applied hydraulic pressure was increased, the yield point also increased. From this information, it would be better to form a full size prepreg at lower applied pressure as the material will flow and form better in the tool under such conditions.

One of skill in the art will readily appreciate the scope of the invention from the foregoing and the claims here below, and that the invention includes all disclosed embodiments, modifications of these that are obvious to a person of skill in the art, and the equivalents of all embodiments and modifications, as defined by law.

What is claimed is:

1. An apparatus for testing the tensile load bearing properties of an uncured prepreg composite material, the apparatus comprising:
   (j) a housing comprising a cavity sized for at least partially containing an uncured prepreg sample to be tested;
   (k) an expandable bladder at least partially contained in the housing; and
   (l) a block located at least partially within the housing and interposed between the bladder and the cavity for containing an uncured prepreg sample to be tested, the block urged towards the cavity to apply pressure to the sample when the apparatus is in use.

2. The apparatus of claim 1, further comprising a heater located at least partially within the housing for controlled heating of the sample to be tested, when the apparatus is in use.

3. The apparatus of claim 1, wherein the cavity comprises four surrounding walls, three of the walls comprised of inner sides of the housing and a fourth wall comprised of a side of the block, the side of the block applying pressure to a sample in the cavity, when the bladder is inflated and the apparatus is in use.

4. The apparatus of claim 2, further comprising release film interposed between the block and an uncured prepreg sample to be tested, and between the heater and the sample to be tested, when the apparatus is in use, to prevent adhesion of the sample to the block or the heater, respectively.

5. The apparatus of claim 1, wherein the housing is substantially rectangular in longitudinal cross section and substantially rectangular in horizontal cross section, the interior of the housing comprising a longitudinal cavity for receiving an uncured prepreg sample to be tested.

6. The apparatus of claim 5, wherein the bladder comprises first and second opposing faces, and wherein the bladder is disposed adjacent one side of the housing such that the first face of the bladder extends substantially coextensively along that side, when the bladder is inflated.

7. The apparatus of claim 6, further comprising a block within the housing, the block comprising first and second opposing sides, the second side of the block extending substantially coextensively with the second face of the bladder, when the bladder is inflated; the first side of the block defining a boundary of the cavity, and the second side of the block in pressure transmitting communication with the second face of the bladder, the block urged by the bladder towards the cavity as the bladder is inflated to thereby apply pressure to a sample in the cavity, when the apparatus is in use.

8. The apparatus of claim 1, wherein the heater comprises heating tape.

9. The apparatus of claim 8, further comprising at least one thermocouple in proximity to of an uncured prepreg sample to measure a temperature of the sample when the apparatus is in use.

10. An apparatus for testing the tensile load bearing properties of a sample of an uncured prepreg composite material, the apparatus comprising:
   (a) a substantially rectangular housing comprising an internal cavity for receiving a sample to be tested;
   (b) a bladder comprising first and second opposing faces, the bladder located within the housing adjacent one inner side of the housing such that the first face of the bladder extends substantially coextensively along that one inner side, when the bladder is inflated;
   (c) a substantially rectangular block within the housing, the block comprising first and second opposing sides, the second side of the block extending substantially coextensively with the second face of the bladder, when the bladder is inflated; the first side of the block defining a wall of the cavity, and the second side of the block in pressure transmitting communication with the second face of the bladder, the block urged by the bladder towards the cavity, as the bladder is inflated, to thereby apply pressure to a sample in the cavity, when the apparatus is in use.

11. The apparatus of claim 10, further comprising a heater for applying controlled heat to a sample in the cavity, when the apparatus is in use.

12. The apparatus of claim 10, further comprising at least one thermocouple located to measure a temperature of a sample, when the apparatus is in use.

13. A method of testing a property of an uncured prepreg sample, the method comprising:
   (a) selecting an uncured prepreg sample to be tested;
   (b) preparing the sample, including optionally applying a release film to the sample;
   (c) subjecting the sample to heat and pressure in an apparatus comprising: a housing sized for at least partially containing the sample to be tested; an expandable bladder at least partially contained in the housing, the bladder applying controlled pressure against a block which in turn transmits applied pressure to the sample; and a heater configured to supply controlled heat to the sample;

(d) measuring a temperature of the sample;

(e) applying tensile force to the sample; and (f) determining the tensile load at which the sample yields.

14. The method of claim 13, wherein the applying of heat comprises applying heat to raise sample temperature to from about 100 to about 350° F.

15. The method of claim 13, wherein the applying of tensile force comprises applying from about 50 psi to about 2000 per inch.

16. The method of claim 13, wherein the preparing of the sample comprises:

cutting the sample to size, applying a release film to the sample, wrapping the release film-covered sample in heating tape, and applying an outer release film to prevent adhesion of the sample to the block.

17. The method of claim 13, wherein the measuring comprises measuring temperature with a thermocouple adjacent or in contact with the sample.

18. The method of claim 13, wherein the prepreg sample comprises filler material selected from continuous, discontinuous, woven, or nonwoven fiber.

19. The method of claim 13, wherein the applying of tensile force comprises applying force at opposed ends of the sample when the sample is at a desired temperature and pressure.

* * * * *